United States Patent [19]

Muchowski et al.

[11] Patent Number: 4,496,577
[45] Date of Patent: Jan. 29, 1985

[54] IMIDAZOLIDINONE PROSTAGLANDINS, COMPOSITIONS AND USE

[75] Inventors: Joseph M. Muchowski, Sunnyvale, Calif.; Angel Guzman, Estro, Mexico

[73] Assignee: Syntex (U.S.A.) Inc., Palo Alto, Calif.

[21] Appl. No.: 539,197

[22] Filed: Oct. 5, 1983

[51] Int. Cl.³ .................. A61K 31/415; C07D 233/02
[52] U.S. Cl. .................................... 514/392; 548/318; 548/321
[58] Field of Search ................ 548/318, 321; 424/273 R

[56] References Cited

U.S. PATENT DOCUMENTS 2,430,006  11/1947  Duschinsky .......................... 548/321

*Primary Examiner*—Robert W. Ramsuer
*Attorney, Agent, or Firm*—James M. Kanagy; Tom M. Moran

[57] ABSTRACT

This invention relates to novel imidazolidinone prostaglandin compounds of the formula

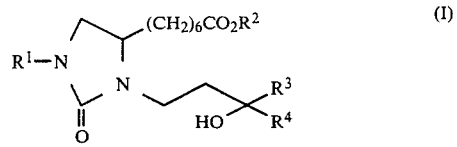

and the pharmaceutically acceptable salts thereof, wherein $R^1$ and $R^2$ are independently hydrogen or alkyl of 1 to 4 carbons; $R^3$ is hydrogen or methyl; and $R^4$ is $-(CH_2)_nCH_3$ wherein n is 3-7, cycloalkyl of 5-7 carbons, a substituent of the formula

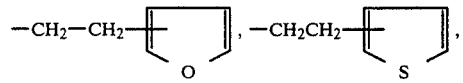

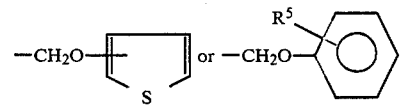

wherein $R^5$ is hydrogen, alkyl of 1 to 4 carbons, alkoxy of 1 to 4 carbons, halo or trifluoromethyl. These compounds are inhibitors of blood platelet aggregation.

12 Claims, No Drawings

IMIDAZOLIDINONE PROSTAGLANDINS, COMPOSITIONS AND USE

BACKGROUND OF THE INVENTION

This invention relates to hetero atom containing prostaglandin type compounds. More particularly it relates to prostaglandin type compounds wherein the five membered ring is an imidazolidinone ring.

Scope of the Invention

The compounds herein are inhibitors of blood platelet aggregation of the formula

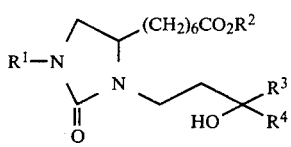

and the pharmaceutically acceptable salts thereof, wherein $R^1$ and $R^2$ are independently hydrogen or alkyl of 1 to 4 carbons; $R^3$ is hydrogen or methyl; and R4 is $-(CH_2)_nCH_3$ wherein n is 3–7, cycloalkyl of 5–7 carbons, a substituent of the formula

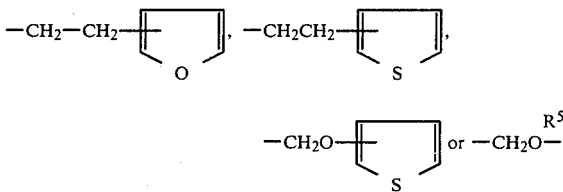

wherein $R^5$ is hydrogen, alkyl of 1 to 4 carbons, alkoxy of 1 to 4 carbons, halo or trifluoromethyl.

Preferred compounds are those wherein $R^3$ is hydrogen and $R^4$ is cycloalkyl, $-(CH_2)_nCH_3$ or

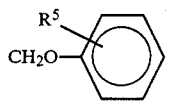

More preferred are those compounds wherein cycloalkyl has 6 carbons, $-(CH_2)_nCH_3$ wherein n is 4–5 and $R^5$ is halo or alkyl. Most preferred are the compounds:

$N^1$-(3-hydroxy-3-cyclohexylpropyl)-5-(6-carboxyhexyl)-imidazolidinone;

$N^1$-(3-hydroxy-4-phenoxybutyl)-5-(6-carboxyhexyl)-imidazolidinone;

$N^1$-(3-hydroxyheptyl)-5-(6-carboxyhexyl)imidazolidinone;

$N^1$-(3-hydroxyoctyl)-5-(6-carboxyhexyl)imidazolidinone; and $N^1$-(3-hydroxynonyl)-5-(6-carboxyhexyl)imidazolidinone.

DEFINITIONS

Halo refers to fluro, bromo or chloro. The phrase "alkyl of 1 to 4 carbons" refers to a radical comprised of carbon and hydrogen which is fully saturated and is exemplified by methyl, ethyl, n-propyl, isopropyl, n-butyl, t-butyl, and the like. Cycloalkyl of 5 to 7 carbon atoms refers to a fully saturated alkane ring exemplified by the pentyl, hexyl and heptyl ring structures. Alkoxy of 1 to 4 carbon atoms encompasses the group —OR wherein R is alkyl of 1 to 4 carbons as defined herein above.

The term "pharmaceutically acceptable salts" refers to the carboxylic acid salts which retains the biological effectiveness and properties of the free acid and which are not biologically or otherwise unsuitable.

Salts derived from inorganic bases include sodium, potassium, lithium, ammonium, calcium, ferrous, ferric, aluminum, zinc, cuprous, cupric, manganous, manganic and the like. Particularly preferred are the ammonium, potassium, sodium, calcium and magnesium salts. Salts derived from pharmaceutically acceptable non-toxic organic basis includes salts of primary, secondary and tertiary amines. Substituted amines include naturally occurring substituted amines, cyclic amines and basic ion exchange resins, such as isopropylamine, trimethylamine, diethylamine, triethylamine, tripropylamine, ethanolamine, 2-dimethylamino ethanol, 2-diethylamino ethanol, tromethamine, lysine, arginine, histidine, caffeine, procaine, hydrabamine, choline, betaine, ethylene diamine, glucosamine, N-methyl glucamine, theobromine, purines, piperazine, piperidine, N-ethyl piperidine, polyamine resins and alike. Particularly preferred are non-toxic organic basis are isopropylamine, diethylamine, ethanolamine, piperidine, tromethamine, choline, and caffeine.

The carboxylic acid salt derivatives of the compounds of Formula I are prepared by treating the corresponding free acids of the compounds of Formula I with at least one molar equivalent of a pharmaceutically acceptable base. Representative pharmaceutically acceptable bases are sodium hydroxide, potassium hydroxide, ammonium hydroxide, calcium hydroxide, trimethylamine, lysine, caffeine, and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, or dioxane. The molar ratio of compounds of Formula I to base used are chosen to provide the ratio desired for any particular salt.

These novel compounds possess asymetric centers and thus can be produced as racemic "(dl)" mixtures or as individual enantiomers. The racemic mixtures can be resolved as desired at appropriate stages by methods known to those skilled in the art, to obtain their respective individual enantiomers.

The compounds of Formula I contain two chiral centers, the ring carbon to which the 7-carbon carboxyl containing chain is attached, and the carbon containing the hydroxyl group.

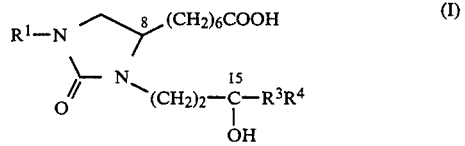

Following the conventional numbering system of prostaglandins, the chiral centers are at carbons 8 and 15.

Accordingly, the compounds of Formula I may exist in a total of four stereoisemeric forms. The present invention is intended to include all such forms and mixtures thereof. The end products of Reaction Scheme 1 will be a mixture of all four stereoisemers unless separation is effected. These mixtures may be resolved, if desired, into individual stereoisemers using conventional means as further outlined hereinbelow.

Diastereomers may, of course, be separated by standard techniques for chemical compounds in general, such as fractional crysallization, chromotography, or some combination of these. Ordinarily, such a separation is effected—i.e., into two racemic mixtures: RR/SS and RS/SR. Mixtures of enantiomers may be resolved by converting the compounds of formula I to diastereomeric forms, separating the diastereomers as above, and regenerating compounds of formula I. In the present case, since the compounds are alcohols, a convenient method is to convert them to the diastereomeric esters by reaction with optically active carboxylic acids. The resulting diastereomeric esters may then be separated, and then cleaved, using standard procedures, into the original, but resolved, compounds of Formula I.

These compounds exhibit prostaglandin like biological activity and thus are useful in the treatment of mammals where the use of prostaglandins is indicated. More particularly, these imidazolidinone compounds of Formula 1 are inhibitors of blood platelet aggregation. The compounds of Formula 1 are useful in the treatment and prevention of conditions and diseases relating to or influenced by blood platelet aggregation.

The present compounds can be administered in a wide variety of dosage forms, either alone or in combination with other pharmaceutically compatible medicaments, in the form of pharmaceutical compositions suited for oral or parenteral administration or inhalation. They are typically administered as pharmaceutical compositions consisting essentially of the free acid, salt or ester and a pharmaceutical carrier. The pharmaceutical carrier can be either a solid material, liquid or aerosol, in which the compound is dissolved, dispersed or suspended, and can optionally contain small amounts of preservative and/or pH buffering agents.

The liquid compositions can, for example, be in the form of solutions, emulsions, suspensions, syrups, or elixers. The solid compositions can take the form of tablets, powders, capsules, pills or the like, preferably in unit dose form for simple administration or precise dosage. Solvents which may be used for preparing stable solutions of the subject compounds are, for example, ethanol, low molecular weight PEGs, dimethyl PEGs, triacetin, citrate triacetate, propylene carbonate and the like. Suitable solid carriers include, for example, pharmaceutical grades of starch, lactose, sodium saccharin, talcum, sodium bisulfite, povidone and the like.

The compounds of this invention are prepared by treating with a base a compound of Formula II

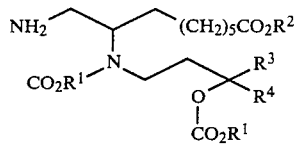

wherein $R^1$ and $R^2$ are alkyl of 1 to 4 carbon atoms and $R^3$ and $R^4$ are defined herein above; or converting an acid of Formula I to an ester, an amide or a pharmaceutically acceptable salt; or converting an ester of Formula I to an acid or pharmaceutically acceptable salt; or converting a salt of the compound of Formula I to another salt; or converting an ester of Formula I to a second ester; or converting the secondary nitrogen in the imidazolidinone ring to a tertiary amine.

PREPARATION AND EXAMPLES

The compounds herein are prepared by treating 2-bromoazelaic acid dimethyl ester with sodium azide; hydrolyzing the the ω-alkyl ester; and reducing the acid to give the alcohol. The synthesis is further carried out by protecting the alcohol; reducing the azido group to the amine; treating the amine with an appropriately substituted vinyl ketone; catalytically reducing the ketone to give the position-15 hydroxyl; treating the aminoalcohol with a urethane forming group; deprotecting the 9-hydroxyl; converting the 9-hydroxyl group to the corresponding mesylate and reacting the latter with sodium azide; catalytically reducing the 9-azido group; and cyclizing the aminourethane groups with base. The resulting imidazolidinone can then be further modified by art known means to give the additional compounds of Formula I.

Schematically, the compounds herein may be prepared by the outline of Reaction Scheme 1.

REACTION SCHEME 1

Steps 1–4

4,496,577
REACTION SCHEME 1
-continued
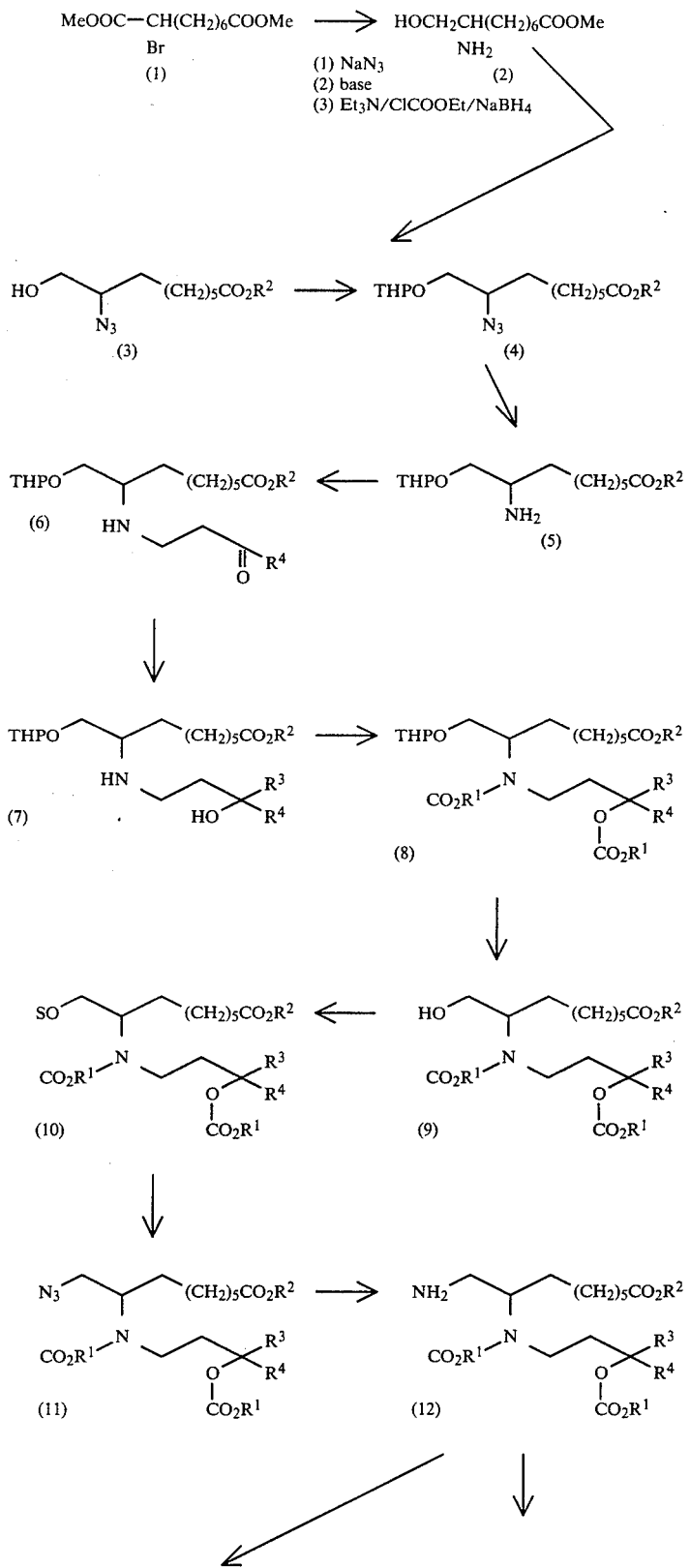

REACTION SCHEME 1
-continued

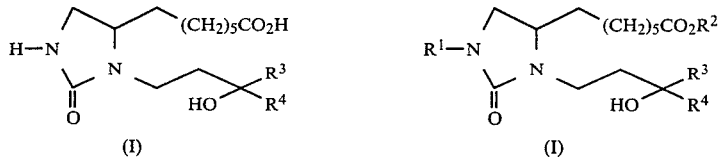

The designation S in compound 10 refers to a sulfonate group, e.g., a mesylate or tosylate group.

The compound of formula 1 can be prepared by the bromination of a dialkyl ester of azelaic acid by means well known in the art. The 2-bromo compound is also commercially available.

In Step 1, a large molar excess of sodium azide, preferably a 4 to 5 molar excess, is added to a solution of the 2-bromo dialkyl ester in an inert, aprotic solvent such as, for example, acetonitrile, or tetrahydrofuran, and the mixture is heated at 50° C. to 120° C., preferably the reflux temperature of the solvent, for two to ten hours, preferably three to four hours.

In Step 2, the compound of formula 1A is dissolved in an aqueous alcohol such as, for example, aqueous ethanol or methanol, preferably aqueous methanol, and a base, such as, for example, sodium hydroxide, potassium carbonate, or sodium carbonate, preferably potassium carbonate, is added in slight excess, preferably a 1.2 to 2 molar excess, with respect to the compound of formula 1A. The mixture is then stirred at 5° C. to 30° C., preferably room temperature, for about 1 to 10 hours, preferably for about 3 to 4 hours. The resulting position-9 mono acid is designated formula 1B.

Then, in Step 3, the mono acid of formula 1B is reduced to the corresponding mono alcohol, designated formula 1C, by means of a metal hydride.

In conducting Step 3, the acid is treated with a slight molar excess excess of tertiary amine such as, for example, triethylamine in an inert aprotic organic solvent, and cooled to −0° C. to 10° C., preferably 0° C., with stirring. An equi-molar amount (approximately) of a reagent to convert the carboxylic acid to the anhydride, preparatory to its reduction is then added. Ethyl chloroformate is the preferred reagent. The mixture is kept cool for 1 to 2 hours, and filtered for clarification if necessary. The filtrate is then treated with a slight excess of a suitable metal hydride, preferably sodium borohydride, and kept at room temperature for 1 to 6 hours, preferably 2 hours.

The alcohol of formula 3 is protected, preferably by converting it to an ether. For example, the alcohol may be treated with 2,3-dihydropyran in the presence of an acid catalyst such as toluenesulfonic acid by adding about a 20% molar excess of the 2,3-dihydropyran to a chilled solution of the alcohol and a dry solvent such as methylene chloride which contains the acid catalyst. The reaction will be carried out at a temperature between about minus 10° to +10° C., preferably at about 0° C. for a period between about 30 minutes and 2 hours, preferably about 1 hour.

The recovered product is then subjected to catalytic hydrogenation in order to reduce the azide group. The reduction preferably will be carried out by means of a transition metal catalyst such as, for example, 10% palladium on charcoal in a simple alcohol such as methanol under hydrogen at elevated pressure.

The resulting amine, formula 5, is then treated with a substituted vinyl ketone in the presence of 1,1,3,3-tetramethylguanidine in a dry, dipolar aprotic solvent at a temperature between about 20°–40° C. for a period of between 1–4 hours. When the initial reaction period is completed, the ketone is reduced in situ by adding a reducing agent such as sodium borohydride directly to the reaction pot without attempting to isolate the ketone. The reduction reaction is effected at a temperature ranging between about −10° to 20° C. The reduction is effected at this reduced temperature in about 30 minutes to 2 hours. Preparation of the Formula 5 compounds will preferably be carried out by employing a 10% excess of the substituted vinyl ketone in a dry solvent such as tetrahydrofuran. The reaction is effected at room temperature in a period of about 2 hours. The reaction mixture is then added to a solution of sodium borohydride (2 molar equivalents) in methanol at 0° C. This solution is stirred for about an additional hour to give the alcohol of formula 7 as a mixture of diasterisomeric racemates.

The 8-position amine compound, formula 7, is converted to the urethane of formula 8 by treating the amine with a three-fold molar excess of ethyl chloroformate or a related chloroformate ester. The reaction is affected by dissolving the amine in a solvent such as pyridine at a temperature between −10° and +10° C., preferably 0° C. and adding ethyl chloroformate with stirring. This solution is then warmed to about room temperature and stirred for up to 24 hours, preferably about 18 hours to complete the reaction.

In order to effect the intramolecular cyclization which gives the imidazolidinone ring, the hydroxyl protecting group must be removed, preferably by means of an aqueous organic acid such as, for example, a mixture of glacial acetic acid; tetrahydrofuran; and water at room temperature for a period of about 24 hours.

The resultant alcohol is then converted into the azido compound as follows: The alcohol is dissolved in a dry solvent such as methylene chloride and cooled to between −10° to +10° C., preferably 0° C. An excess of a trialkylamine, for example, about 2.6 molar equivalents of triethylamine, and a 30% molar excess of an alkyl sulfonyl chloride, for example, methanesulfonyl chloride are added. The reaction is usually completed in about 15 minutes to an hour, more specifically about 30 minutes.

The mesylate of formula 10 is recovered as a crude extract and, without further purification, diluted with a polar solvent such as acetonitrile and treated with a large excess of sodium azide (ca. 10 molar equivalents). The mixture is initially stirred for about 30 minutes to 2 hours, preferably about 1 hour, at room temperature and then refluxed for about 2 hours to afford the azido compound.

The purified azide of formula 11 is then subjected to catalytic reduction to obtain the amine of formula 12. The reduction is carried out in the same manner as used previously to reduce the position-8 azido group by the use of a transition metal catalyst such as 10% palladium on charcoal, the solvent being a simple alcohol such as methanol. The reaction is carried out at room temperature under hydrogen at an elevated pressure, i.e., about 40 psi until no more hydrogen is absorbed.

Treating the amine of formula 12 with a base effects formation of the imidazolidinone ring. The amine is dissolved in a solvent made up of a simple alcohol such as methanol and water to which is added about a twofold excess of a strong base such as sodium hydroxide. A 16 to 20 hour reflux, preferably about 18 hours effects formation of the imidazolidinone ring while also hydrolyzing the esters at position-1 and 15. The acid may be recovered or may be converted back to an ester for further purification and characterization. If the ester is to be made, the crude product from the foregoing reaction is treated with diazomethane in a solvent such as ether to give the methyl ester.

A further understanding of the invention may be had from the following non-limiting preparations and examples.

PREPARATION 1

Dimethyl 2-azidoazelate

Sodium azide (4.87 g, 75 mmol) was added to a solution of dimethyl 2-bromoazelate (5.9 g, 20 mmol) prepared according to Auguston, M, et al; *Acta Chim. Acad. Sci. Hung;* 46:85 (1965) in acetonitrile, and the mixture was heated at reflux temperature for 4 h. The solvent was removed in vacuo, dichloromethane (80 ml) was added to the residue, and the mixture was washed with water. The organic phase was dried over sodium sulfate and the solvent was removed in vacuo to give the title compound as an oil.

IR: ($CHCl_3$), 2070, 1735 $cm^{-1}$.
NMR: ($CDCl_3$), 2.27 (t, 2H), 3.62 (s, 3H), 3.75 (s, 3H), 3.75 (t, 1H).
CIMS($NH_3$) 275 $(M-NH_4)^+$

PREPARATION 2

2-Azido-8-methoxycarbonyloctanoic acid

Potassium carbonate (0.414 g, 3 mmol) was added to a solution of the azide prepared in Preparation 1 (0.642 g, 2.5 mmol) in 25% aqueous methanol (20 ml) and the mixture was stirred at room temperature for 3 h. Water (10 ml) was added and the solution was extracted with dichloromethane (40 ml). The aqueous phase was made acidic with oxalic acid and the product was extracted with dichloromethane (4×30 ml). The extract was dried over sodium sulfate and evaporated in vacuo to give the 2-azido-7-methoxycarbonyloctanoic acid as an oil.

IR: ($CHCl_3$), 2080, 1730 $cm^{-1}$.
NMR: ($CDCl_3$), 2.30 (t, 2H), 3.64 (s, 3H), 3.85 (t, 1H).
CIMS ($NH_3$) 261 $(M-NH_4)^+$

PREPARATION 3

2-Azido-8-methoxycarbonyloctan-1-ol

Triethylamine (0.412 g, 4.08 mmol) was added to a stirred solution of the carboxylic acid from Preparation 2 (0.850 g, 3.4 mmol) in anhydrous tetrahydrofuran (40 ml). The mixture was stirred for 5 min., cooled to 0° C., and ethyl chloroformate (0.422 g, 4.08 mmol) was added thereto. After stirring for 1.5 h at 0°, the temperature was left to reach ambient and then the mixture was filtered. The filtrate was added to a mixture of sodium borohydride (0.155 g) and 30% aqueous tetrahydrofuran (5 ml). After 45 min. at room temperature, the mixture was diluted with water (40 ml) and extracted with dichloromethane (4×40 ml). The extract was washed over sodium sulfate and evaporated in vacuo. The residue was subjected to tlc using hexane-ethyl acetate (3:2) as the developing solvent. The 2-azido-7-methoxycarbonyl octan-1-ol was obtained as an oil.

IR: ($CHCl_3$), 3480, 2070, 1730 $cm^{-1}$.
NMR: ($CDCl_3$), 1.25–1.70 (m, 10H), 2.27 (t, 2H), 3.40–3.60 (m, 3H), 3.13 (s, 3H).

PREPARATION 4

8-Azido-9-tetrahydropyran-2-yloxynonanoic acid methyl ester

To a cold solution 8.5 g (37.0 mmoles) of the alcohol from Preparation 3 in 50 ml of dry methylene chloride and 90 mg of p-toluenesulfonic acid was added 4 ml (44.7 mmoles) of freshly distilled 2,3-dihydropyran. The mixture was stirred at 0° C., and the reaction was followed by t.l.c. (hexane:ethyl acetate 75:25). After an hour, the reaction was complete. The mixture was diluted with 100 ml of methylene chloride, washed with a 5% solution of sodium bicarbonate (25 ml) and with water. The organic phase was dried ($MgSO_4$) and concentrated in vacuo. The residue was purified by silica gel column chromatography. The product was eluted with 10% ethyl acetate in hexane, to provide the title compound as an oil.

IR: ($CHCl_3$), 2070, 1735 $cm^{-1}$.
NMR: ($CDCl_3$), 2.31 (t,J=6 Hz, 2H), 3.44 (m, −2H), 3.64 (s, 3H), 3.83 (m, 3H), 4.64 (s, 1H).

PREPARATION 5

8-Amino-9-tetrahydropyran-2-yloxynonanoic acid methyl ester

A mixture of 10.57 g (33.72 mmoles) of the azido compound from Preparation 4 and 2 g. of 10% palladium on charcoal catalyst in 100 ml of methanol was stirred under hydrogen at 40 psi. When no more hydrogen was absorbed the reaction mixture was filtered and evaporated to dryness under vacuum to provide the title compound as an oil.

IR: ($CHCl_3$) 3400, 1735 $cm^{-1}$.
NMR: ($CDCl_3$), 2.06 (s, 2H), 2.3 (t, J=6 Hz 2H), 2.76–3.6 (m, 3H), 3.66 (s, 3H), 3.83 (m, 2H), 4.56 (s, 1H).
M.S.: 288 ($MH^{30}$).

PREPARATION 6

8-[(3-hydroxy-3-cyclohexylpropyl)amino]-9-tetrahydropyran-2-yloxynonanoic acid methyl ester A mixture of 9.1 g (31.66 mmoles) of the Preparation 5 amine, 4.82 g (34.8 mmoles) of cyclohexyl vinyl ketone and 1 ml of 1,1,3,3-tetramethylguanidine in 40 ml of dry tetrahydrofuran was stirred at room temperature for 2 hours, and then was added to a cold solution of 2.4 g (2 molar equivalents) of sodium borohydride in 100 ml of methanol. The reaction was stirred for an additional hour and then it was diluted with methylene chloride (200 ml), washed with brine (75 ml) dried over $MgSO_4$ and evaporated under vacuum. The residue was purified by silica gel column chromatography using as eluent a mixture of $CH_2Cl_2$:MeOH:$NH_4OH$ (15:10:1) to provide the title compound as diasterisomeric racemates.

Oil

IR: (CHCl$_3$) 3250, 1735 cm$^{-1}$.

NMR: (CDCl$_3$), 2.3 (t, J=6 Hz, 2H), 2.73 (m, 2H), 2.9–3.26 (m, 1H), 3.56 (m, 5H), 3.66 (s, 3H), 3.83 (m, 1H), 4.53 (s, 1H).

Proceeding in a similar manner, but substituting for cyclohexyl vinyl ketone the appropriate vinyl ketone, there may be prepared the following compounds:

8-[(3-hydroxy-3-cyclopentylpropyl)amino]-9-tetrahydropyran-2-yloxynonanoic acid methyl ester;
8-[(3-hydroxyhexyl)amino]-9-tetrahydropyran-2-yloxynonanoic acid methyl ester;
8-[(3-hydroxyheptyl)amino]-9-tetrahydropyran-2-yloxynonanoic acid methyl ester;
8-[(3-hydroxyoctyl)amino]-9-tetrahydropyran-2-yloxynonanoic acid methyl ester;
8-[(3-hydroxynonyl)amino]-9-tetrahydropyran-2-yloxynonanoic acid methyl ester;
8-[(3-hydroxydodecyl)amino]-9-tetrahydropyran-2-yloxynonanoic acid methyl ester;
8-[(3-hydroxy-4-phenoxybutyl)amino]-9-tetrahydropyran-2-yloxynonanoic acid methyl ester;
8-[(3-hydroxy-4-(4-chlorophenoxy)butyl)amino]-9-tetrahydropyran-2-yloxynonanoic acid methyl ester;
8-[(3-hydroxy-4-(4-fluorophenoxy)butyl)amino]-9-tetrahydropyran-2-yloxynonanoic acid methyl ester;
8-[(3-hydroxy-4-(2-chlorophenoxy)butyl)amino]-9-tetrahydropyran-2-yloxynonanoic acid methyl ester;
8-[(3-hydroxy-4-(2-fluorophenoxy)butyl)amino]-9-tetrahydropyran-2-yloxynonanoic acid methyl ester;
8-[(3-hydroxy-4-(2,4-dichlorophenoxy)butyl)amino]-9-tetrahydropyran-2-yloxynonanoic acid methyl ester;
8-[(3-hydroxy-4-(2,4-difluorophenoxy)butyl)amino]-9-tetrahydropyran-2-yloxynonanoic acid methyl ester;
8-[(3-hydroxy-4-(2,4,6-trifluorophenoxy)butyl)amino]-9-tetrahydropyran-2-yloxynonanoic acid methyl ester;
8-[(3-hydroxy-4-(4-trifluoromethylphenoxy)butyl)amino]-9-tetahydropyran-2-yloxy]nonanoic acid methyl ester;
8-[(3-hydroxy-4-(4-methylphenoxy)butyl)amino]-9-tetrahydropyran-2-yloxynonanoic acid methyl ester;
8-[(3-hydroxy-4-(4-butylphenoxy)butyl)amino]-9-tetrahydropyran-2-yloxynonanoic acid methyl ester;
8-[(3-hydroxy-4-(4-propylphenoxy)butyl)amino]-9-tetrahydropyran-2-yloxynonanoic acid methyl ester;
8-[(3-hydroxy-4-(2-methylphenoxy)butyl)amino]-9-tetrahydropyran-2-yloxynonanoic acid methyl ester;
8-[(3-hydroxy-4-(2-butylphenoxy)butyl)amino]-9-tetrahydropyran-2-yloxynonanoic acid methyl ester;
8-[(3-hydroxy-4-(2,4-dimethylphenoxy)butyl)amino]-9-tetrahydropyran-2-yloxynonanoic acid methyl ester;
8-[(3-hydroxy-4-(2,4,6-trimethylphenoxy)butyl)amino]-9-tetrahydropyran-2-yloxynonanoic acid methyl ester;
8-[(3-hydroxy-4-(4-methoxyphenoxy)butyl)amino]-9-tetrahydropyran-2-yloxynonanoic acid methyl ester;
8-[(3-hydroxy-4-(4-butyloxyphenoxy)butyl)amino]-9-tetrahydropyran-2-yloxynonanoic acid methyl ester;
8-[(3-hydroxy-4-(2-methoxyphenoxy)butyl)amino]-9-tetrahydropyran-2-yloxynonanoic acid methyl ester;
8-[(3-hydroxy-4-(2,4-dimethoxyphenoxy)butyl)amino]-9-tetrahydropyran-2-yloxynonanoic acid methyl ester;
8-[(3-hydroxy-5-fur-2-yl pentyl)amino]-9-tetrahydropyran-2-yloxynonanoic acid methyl ester;
8-[(3-hydroxy-5-fur-3-yl pentyl)amino]-9-tetrahydropyran-2-yloxynonanoic acid methyl ester;
8-[(3-hydroxy-5-thien-2-yl pentyl)amino]-9-tetrahydropyran-2-yloxynonanoic acid methyl ester; and
8-[(3-hydroxy-5-thien-3-yl pentyl)amino]-9-tetrahydropyran-2-yloxynonanoic acid methyl ester.

PREPARATION 7

8-(N-(3-ethoxycarbonyloxy-3-cyclohexylpropyl)-N-ethoxycarbonyl)amino-9-tetrahydropyran-2-yloxynonanoic acid methyl ester A solution of 9.0 g (21 mmoles) of the Preparation 6 compound in 100 ml of pyridine was cooled to 0° C. To this stirred mixture was added 6 ml (62.9 mmoles) of ethyl chloroformate. Stirring was continued at room temperature for 18 hours. The solvent was evaporated under vacuum and the residue taken up in methylene chloride (200 ml), washed with brine (60 ml), dried (MgSO$_4$) and evaporated to dryness. The residue was purifed by silica gel column chromatography using 20% ethyl acetate in hexane as the eluent. Appropriate fractions were combined and the solvent removed to give the title compound as an oil. (A racemic mixture.)

IR: (CHCl$_3$) 1735, 1685 cm$^{-1}$.

NMR: (CDCl$_3$), 2.27 (t, J=6 Hz, 2H), 3.0–3.56 (m, 4H), 3.66 (s, 3H), 3.83 (m, 1H), 4.1–4.2 (2 quartets 4H), 4.53 (m, 2H).

PREPARATION 8

8-(N-(3-ethoxycarbonyloxy-3-cyclohexylpropyl)-N-ethoxycarbonyl)amino-9-hydroxynonanoic acid methyl ester The compound recited in preparation 7, 4.45 g (7.78 mmoles) was stirred for 24 hours in 50 ml of a mixture of acetic acid:THF:H$_2$O (3:1:1). The solvent was removed under reduced pressure and the residue purified by silica gel column chromatography. The product was eluted with 30% of ethyl acetate in hexane giving the title compound as a mixture of diasterioisomeric racemates.

Oil

IR: (CHCl$_3$) 3450, 1740 cm$^{-1}$.

NMR: (CDCl$_3$) 2.3 (t, J=6 Hz, 2H) 3.2 (m, 2H) 3.66 (s, 3H) 4.1–4.2 (2 quartets, 4H) 4.53 (quartet 1H)

MS 488 (MH+).

PREPARATION 9

8-(N-(3-ethoxycarbonyloxy-3-cyclohexylpropyl)-N-ethoxycarbonyl)amino-9-azidononanoic acid methyl ester A solution of 2.48 g (5.08 mmoles) of the 9-hydroxy compound from preparation 8 in 50 ml dry methylene chloride was cooled to 0° C., then 1.33 g (2.6 molar equiv) of methanesulfonyl chloride were added. The reaction was stirred for 30 min at 0° C. and then diluted with methylene chloride (75 ml), washed with brine (40 ml), dried with MgSO$_4$ and the solvent evaporated under vacuum. The crude mesylate was diluted with 30 ml of acetonitrile and treated with 3 g (46 mmoles) of sodium azide. The mixture was stirred for an hour at room temperature and then under reflux for two hours more. The mixture was cooled, diluted with methylene chloride (75 ml), washed with water, dried (MgSO$_4$) and concentrated under vacuum. The residue was purified by silica gel column chromatography. The product was eluted with 10% ethyl acetate in hexane to provide the title compound as a mixture of diasterioisomeric racemates.

Oil

IR: (CHCl$_3$) 2065, 1738, 1690 cm$^{-1}$.

NMR: (CDCl$_3$), 2.3 (t, J=6 Hz, 2H), 3.0–3.4 (m, 4H), 3.66 (s, 3H), 3.83 (m, 1H), 4.12–4.2 (2 quartets, 4H), 4.53 (quartet 1H).

MS: 513 (MH+).

EXAMPLE I 8-(N-(3-ethoxycarbonyloxy-3-cyclohexylpropyl)-N-ethoxycarbonyl)amino-9-aminononanoic acid methyl ester A mixture of 1.9 g (3.7 mmoles) of the position 9 azido compound from Preparation 9 and 200 mg of 10% palladium on charcoal catalyst in 40 ml of methanol was stirred under hydrogen atmosphere at 40 psi until no more hydrogen was absorbed. The reaction mixture was filtered and evaporated to dryness under vacuum, to provide the title product (mixture of diasterioisomeric racemates).

Oil

IR: (CHCl$_3$) 1740, 1690 cm$^{-1}$.

NMR: (CDCl$_3$), 2.3 (t, J=6 Hz), 2.8 (m, 4H), 3.16 (m, 2H), 3.66 (s, 3H), 4.1–4.2 (2 quartets, 4H), 4.5 (quartet 1H).

EXAMPLE II 1-(3-hydroxy-3-cyclohexylpropyl)-5-(6-methoxycarbonylhexyl)imidazolidinone The diamine compound of Example I, 1.25 g (2.5 mmoles) was dissolved in a mixture of 15 ml of methanol, 4 ml of water and 410 mg (4 molar equivalents) of sodium hydroxide and the mixture was refluxed for 18 hours. The solvent was removed under vacuum. The residue was diluted with water (15 ml), acidified with concentrated hydrochloric acid and extracted with (2×40 ml) ethyl acetate. The organic extracts were washed with water dried (MgSO$_4$) and evaporated to dryness. The crude product was then treated with 50 ml of a diazomethane solution in ether. After evaporation of the ether, the residue was purified by preparative tlc to provide the title compound as a mixture of diasterioisomeric racemates.

Oil

IR: (CHCl$_3$) 3400, 1730, 1680 cm$^{-1}$.

NMR: (CDCl$_3$), 2.3 (t, J=6 Hz), 3.1 (m, 2H), 3.46 (m, 2H), b 3.66 (s, 3H), 4.06 (m, 1H), 4.96 (s, 1H),

MS: 368 (M+).

EXAMPLE III 1-(3-hydroxy-3-cyclohexylpropyl)-5-(6-carboxyhexyl)imidazolidinone A solution of 488 mg (1.32 mmoles) of the imidazolidinone from Example II in 5 ml of methanol was stirred for 20 hours with 4 ml of 0.5N aqueous sodium hydroxide solution. The solvent was evaporated under vacuum, the residue dissolved in 10 ml of water and acidified with concentrated hydrochloric acid. The product was extracted (2×25 ml) with methylene chloride, dried (MgSO$_4$) and evaporated to yield the title compound (mixture of diasterioisomeric racemates).

Oil

IR: (CHCl$_3$) 3360, 1700 cm$^{-1}$.

NMR: (CDCl$_3$), 2.33 (t, J=6 Hz, 2H), 3.1 (m, 2H), 3.53 (m, 2H), 4.00 (m, 1H), 5.76 (s, 1H), 6.2 (s, 1H).

MS: 354 (M+).

By following the reaction conditions of Preparation 7-9 and Examples I–III, the compounds prepared as per Preparation 6 are converted to the imidazolidinone of this, Example III, exemplified by the following compounds:

$N^1$-(3-hydroxy-3-cyclopentylpropyl)-5-(6-carboxyhexyl)imidazolidinone;

$N^1$-(3-hydroxy-3-cycloheptylpropyl)-5-(6-carboxyhexyl)imidazolidinone;

$N^1$-(3-hydroxyhexyl)-5-(6-carboxyhexyl)imidazolidinone;

$N^1$-(3-hydroxyheptyl)-5-(6-carboxyhexyl)imidazolidinone;

$N^1$-(3-hydroxyoctyl)-5-(6-carboxyhexyl)imidazolidinone;

$N^1$-(3-hydroxydocidyl)-5-(6-carboxyhexyl)imidazolidinone;

$N^1$-(3-hydroxy-4-phenoxybutyl)-5-(6-carboxyhexyl)imidazolidinone;

$N^1$-(3-hydroxy-4-(4-chlorophenoxybutyl)-5-(6-carboxyhexyl)imidazolidinone;

$N^1$-(3-hydroxy-4-(4-fluorophenoxybutyl)-5-(6-carboxyhexyl)imidazolidinone;

$N^1$-(3-hydroxy-4-(2-chlorophenoxybutyl)-5-(6-carboxyhexyl)imidazolidinone;

$N^1$-(3-hydroxy-4-(2-fluorophenoxybutyl)-5-(6-carboxyhexyl)imidazolidinone;

$N^1$-(3-hydroxy-4-(2,4-dichlorophenoxybutyl)-5-(6-carboxyhexyl)imidazolidinone;

$N^1$-(3-hydroxy-4-(2,4-difluorophenoxybutyl)-5-(6-carboxyhexyl)imidazolidinone;

$N^1$-(3-hydroxy-4-(2,4,6-trichlorophenoxybutyl)-5-(6-carboxyhexyl)imidazolidinone;

$N^1$-(3-hydroxy-4-(2,4,6-difluorophenoxybutyl)-5-(6-carboxyhexyl)imidazolidinone;

$N^1$-(3-hydroxy-4-(4-trifluoromethylphenoxy)butyl)-5-(6-carboxyhexyl)imidazolidinone;

$N^1$-(3-hydroxy-4-(4-methylphenoxy)butyl)-5-(6-carboxyhexyl)imidazolidinone;

$N^1$-(3-hydroxy-4-(4-butylphenoxy)butyl)-5-(6-carboxyhexyl)imidazolidinone;

$N^1$-(3-hydroxy-4-(4-propylphenoxy)butyl)-5-(6-carboxyhexyl)imidazolidinone;

$N^1$-(3-hydroxy-4-(2-methylphenoxy)butyl)-5-(6-carboxyhexyl)imidazolidinone;

$N^1$-(3-hydroxy-4-(2-butylphenoxy)butyl)-5-(6-carboxyhexyl)imidazolidinone;

$N^1$-(3-hydroxy-4-(2,4-dimethylphenoxy)butyl)-5-(6-carboxyhexyl)imidazolidinone;

$N^1$-(3-hydroxy-4-(2,4,6-trimethylphenoxy)butyl)-5-(6-carboxyhexyl)imidazolidinone;

$N^1$-(3-hydroxy-4-(4-methoxyphenoxy)butyl)-5-(6-carboxyhexyl)imidazolidinone;

$N^1$-(3-hydroxy-4-(4-butyloxyphenoxy)butyl)-5-(6-carboxyhexyl)imidazolidinone;

$N^1$-(3-hydroxy-4-(2-methoxyphenoxy)butyl)-5-(6-carboxyhexyl)imidazolidinone;

$N^1$-(3-hydroxy-4-(2,4-dimethoxyphenoxy)butyl)-5-(6-carboxyhexyl)imidazolidinone;

$N^1$-(3-hydroxy-5-fur-2-ylpentyl)-5-(6-carboxyhexyl)imidazolidinone;

$N^1$-(3-hydroxy-5-fur-3-ylpentyl)-5-(6-carboxyhexyl)imidazolidinone;

$N^1$-(3-hydroxy-5-thien-2-ylpentyl)-5-(6-carboxyhexyl)imidazolidinone; and $N^1$-(3-hydroxy-5-thien-3-ylpentyl)-5-(6-carboxyhexyl)imidazolidinone.

EXAMPLE IV

An injectable preparation buffered to a pH of 7 is prepared having the following composition:

| Ingredients | |
|---|---|
| Active ingredient | 0.2 mg |
| KH$_2$PO$_4$ buffer (0.4 M solution) | 2 ml |
| KOH (1 N$^1$) | q.s. to ph 7 |
| water (distilled, sterile) | q.s. to 20 ml |

EXAMPLE V

An oral suspension is prepared having the following composition:

| Ingredients | |
|---|---|
| Active ingredient | 0.1 mg |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE IV

In Vitro Human Platelet Aggregation Inhibition

Biological activity of the claimed compounds is tested by in vitro human platelet aggregation assay. This assay determines the effectiveness of the compounds in inhibiting the platelet aggregation.

The assay employs modified turbidimetric methods of Born (*J. Physiol.*, 67P (1962) and Evans et al, *J. Exp. Med.*, 128, 877P (1968), and it is based on the physiological response of the blood platelets to a certain stimuli. In normal circulating blood, platelets are carried along separately from each other and they do not adhere to undamaged endothelium. In response to any direct damage to the vascular wall, however, the blood platelets will start to aggregate. Thus, whenever there occurs an injury causing bleeding, rupture, cut or another type of damage to the vascular wall, the collagen fibers in the wall become exposed and platelets immediately start to adhere to them and begin to form a platelet thrombi. Immediately thereafter, the platelets start to secrete large quantities of adenosine diphosphate (ADP) which, in turn activates the other platelets that adhere to the original platelets and eventually form the plug which closes the rupture of the vascular wall. In medical parlance the first process is called collagen-induced primary platelet aggregation, the second process is called ADP-mediated secondary platelet aggregation. This situation can be artificially simulated by natural platelet aggregation inducers such as collagen, ADP, or arachidonic acid to the human platelet-rich plasma.

Preparation of human platelets-rich plasma

The blood samples used for the assay are collected into sodium citrate anticoagulant of a final concentration of 0.38%. The platelet-rich plasma is collected after centrifugation at 200 rpm at room temperature. To determine whether the platelet-rich plasma needs dilution to obtain optimal optical density, citrated plasma containing $10^{-8}$–$10^{-9}$ platelets per milliliter is pipetted into a Spinco transparent plastic centrifuge tube. The tube is inserted into a Unicam SP 400 absorptiometer and the light at the wave-length of 600 m is passed through the tube. The dark current is set at infinity and the optical density of distilled water at zero. The plasma is stirred by a magnetic stirrer. If necessary, platelet-rich plasma is diluted with 0.154M sodium chloride to obtain appropriate optical density.

Platelet aggregation procedure

Platelet-rich plasma of appropriate optical density is mixed with appropriate concentration of tested compounds to make up 1 ml of mixture of platelet-rich plasma and tested compound. The concentration of each tested compound varied from $1.0 \times 10^{-5}$ moles to $1.0 \times 10^{-9}$ moles. Each concentration is tested individually by number of repetitions varying from 1 to 6. Each sample mixture consisting of platelet-rich plasma and tested compound is incubated for about 3 to 5 minutes under constant stirring at 500 rpm at 30 C. Thereafter, a predetermined optimal concentration of platelet aggregation inducer is added to each sample mixture. Inducers which are used for testing may be chosen from:

1. Collagen Suspension Inducer

Collagen suspension is prepared by dissolving 2 g of commercial collagen (Sigma Chemical Company) in 100 ml of modified Tyrode's solution at 0 C. and homogenized in the Waring blender for a total of 5 minutes. To remove coarse particle matter the mixture is centrifuged at 810 rpm for 10 minutes. The supernatant suspension is then diluted with modified Tyrode's solution to a concentration which produce maximum aggregation of the platelets being tested, but which, on further dilution, cause less than maximum aggregation.

2. Adenosine Diphosphate Inducer

Adenosine Diphosphate (ADP) is purchased from Sigma Chemical Company. ADP inducer solution of final concentration of 5 mol is prepared by dissolving 214 mg of ADP in 1 ml of tris buffer (0.01M at pH 9 at 22 C. 0). Optimal amount of ADP inducer was found to be 5 mol.

3. Arachidonic Acid Inducer

Arachidonic acid (Nu Chek Prep Co.) inducer solution is prepared by dissolving 150–300 g of arachidonic acid in 1 ml of a mixture of 10% of ethanol and 90% of 65.6 mmol of sodium carbonate buffer to achieve concentration 0.5 to 1 mmol.

A tube with the mixture of platelet-rich plasma, tested compound and ADP inducer (5 mol/10 l) is inserted into the absorptiometer and optical density changes are recorded on chart. Aggregation of the platelets is determined from maximal optical density change. Maximal optical density of a mixture of platelet-rich plasma with inducer, but without the tested compounds, is taken as 100% of platelet aggregation. The maximal optical density of the sample mixture of platelet-rich plasma, ADP inducer and appropriate amount of tested compound is compared to the maximal optical density of the sample without tested compound and inhibitory effectiveness of tested compounds is calculated. For each sample the percentage of the platelet aggregation is calculated and if more than one measurement with the same concentration of the tested compounds are done, the final value is expressed as an average of all measurements with ±S.E. The inhibitory concentration is the effective concentration of tested compound which is able to prevent 50% of the platelet aggregation, where, without the tested compound, the platelet aggregation would have been 100%. The Potency of Inhibitor is expressed in relationship to inhibitory effectiveness of $PGE_1$ which is arbitrarily denominated as 1.

The compounds of this invention were tested by this procedure and were found to be active inhibitors of platelet aggregation.

What is claimed is:

1. A compound of the formula $$R^1-N\underset{\underset{O}{\|}}{\overset{}{\diagdown}}\!\!\begin{array}{c}\diagup CH(CH_2)_6CO_2R^2\\ N-CH_2CH_2-C(R^3)(R^4)OH\end{array}$$ (I)

and the pharmaceutically acceptable salts thereof, wherein $R^1$ and $R^2$ are independently hydrogen or alkyl of 1 to 4 carbons; $R^3$ is hydrogen or methyl; and $R^4$ is —$(CH_2)_nCH_3$ wherein n is 3–7, cycloalkyl of 5–7 carbons, a substituent of the formula —CH$_2$—CH$_2$—(furan), —CH$_2$CH$_2$—(thiophene), —CH$_2$O—(thiophene) or —CH$_2$O—(phenyl-R$^5$)

wherein $R^5$ is hydrogen, alkyl of 1 to 4 carbons, alkoxy of 1 to 4 carbons, halo or trifluoromethyl.

2. A compound according to claim 1 wherein $R^3$ is hydrogen and $R^4$ is cycloalkyl.

3. A compound according to claim 2 wherein $R^4$ is cyclohexyl.

4. A compound according to claim 3 which is 1-(3-hydroxy-3-cyclohexylpropyl)-5-(6-methoxycarbonylhexyl)imidazolidinone and its pharmaceutically acceptable salts.

5. A compound according to claim 1 wherein $R^3$ is hydrogen and $R^4$ is —$(CH_2)_nCH_3$ wherein n is 3–7.

6. A compound according to claim 5 wherein n is 4.

7. A compound according to claim 1 wherein $R^3$ is hydrogen and $R^4$ is a substituent of the formula —CH$_2$O—(phenyl-R$^5$)

wherein $R^5$ is as defined in claim 1.

8. A compound according to claim 7 wherein $R^5$ is hydrogen.

9. A compound according to claim 7 wherein $R^5$ is halo.

10. A compound according to claim 7 wherein $R^5$ is alkyl of 1 to 4 carbons.

11. A method of inhibiting platelet aggregation which method comprises administering an effective amount of a compound of claim 1 to a mammal either alone or in add mixture with a pharmaceutically acceptable excipient.

12. A pharmaceutical composition comprising a pharmaceutically acceptable excipient and a compound according to claim 1.

* * * * *